(12) United States Patent
Sumanasinghe

(10) Patent No.: US 11,969,335 B2
(45) Date of Patent: Apr. 30, 2024

(54) WOVEN GRAFT HAVING A TAPER WITH A RE-ENGAGED WARP END

(71) Applicant: Cook Medical Technologies LLC, Bloomington, IN (US)

(72) Inventor: Ruwan Sumanasinghe, Carmel, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 0 days.

(21) Appl. No.: 17/241,808

(22) Filed: Apr. 27, 2021

(65) Prior Publication Data

US 2021/0330445 A1  Oct. 28, 2021

Related U.S. Application Data

(60) Provisional application No. 63/016,662, filed on Apr. 28, 2020.

(51) Int. Cl.
| | | |
|---|---|---|
| *A61F 2/06* | (2013.01) | |
| *A61F 2/07* | (2013.01) | |
| *D03D 3/02* | (2006.01) | |
| *D03D 13/00* | (2006.01) | |

(52) U.S. Cl.
CPC .................. *A61F 2/07* (2013.01); *A61F 2/06* (2013.01); *D03D 3/02* (2013.01); *D03D 13/004* (2013.01); *A61F 2220/0075* (2013.01); *A61F 2250/0039* (2013.01)

(58) Field of Classification Search
CPC ... A61F 2/07; D04B 39/04; D10B 2403/0333; D10B 2509/06; D03D 3/02
See application file for complete search history.

(56) References Cited

U.S. PATENT DOCUMENTS

| | | | |
|---|---|---|---|
| 180,790 | A | 8/1876 | Van Dussen Reed |
| 444,880 | A | 1/1891 | Erskine |
| 2,729,958 | A | 1/1956 | Miles |
| 2,978,787 | A | 4/1961 | Liebig |
| 3,096,560 | A | 7/1963 | Liebig |

(Continued)

FOREIGN PATENT DOCUMENTS

| | | |
|---|---|---|
| CA | 2422915 C | 5/2007 |
| DE | 2913510 A1 | 10/1979 |

(Continued)

OTHER PUBLICATIONS

Buesgen translation of DE 10043291 (Year: 2001).*

(Continued)

*Primary Examiner* — Brian E Pellegrino
(74) *Attorney, Agent, or Firm* — Crowell & Moring LLP

(57) ABSTRACT

A tubular graft may include a first woven layer, where the first woven layer forms a first side of the tubular graft; a second woven layer, where the second woven layer forms a second side of the tubular graft; and a tapered portion having an edge, where the edge connects the first woven layer and the second woven layer, where the tapered portion includes a first weft thread, a second weft thread, and a third weft thread, and where a floating portion of a first warp end extends from the first weft thread to the third weft thread such that the floating portion bypasses the second weft thread.

12 Claims, 11 Drawing Sheets

(56) References Cited

U.S. PATENT DOCUMENTS

| | | |
|---|---|---|
| 3,853,462 A | 12/1974 | Smith |
| 3,945,052 A | 3/1976 | Liebig |
| 4,166,463 A | 9/1979 | Bloom |
| 4,668,545 A | 5/1987 | Lowe |
| 4,771,518 A | 9/1988 | LaPointe et al. |
| 4,822,371 A | 4/1989 | Jolly et al. |
| 5,178,630 A * | 1/1993 | Schmitt .................. D03D 3/02 623/1.33 |
| 5,282,846 A | 2/1994 | Schmitt |
| 5,282,848 A | 2/1994 | Schmitt |
| 5,370,682 A | 12/1994 | Schmitt |
| 5,370,683 A | 12/1994 | Fontaine |
| 5,385,580 A | 1/1995 | Schmitt |
| 5,487,858 A | 1/1996 | Schmitt |
| 5,509,931 A | 4/1996 | Schmitt |
| 5,697,970 A | 12/1997 | Schmitt et al. |
| 5,755,734 A | 5/1998 | Richter et al. |
| 5,800,514 A | 9/1998 | Nunez et al. |
| 5,904,714 A | 5/1999 | Nunez et al. |
| 5,913,894 A | 6/1999 | Schmitt |
| 6,090,137 A | 7/2000 | Schmitt |
| 6,187,033 B1 | 2/2001 | Schmitt et al. |
| 6,280,467 B1 | 8/2001 | Leonhardt |
| 6,454,796 B1 | 9/2002 | Barkman et al. |
| 6,475,232 B1 | 11/2002 | Babbs et al. |
| 6,592,539 B1 | 7/2003 | Finarsson et al. |
| 6,626,938 B1 | 9/2003 | Butaric et al. |
| 6,814,754 B2 | 11/2004 | Greenhalgh |
| 6,974,586 B2 | 12/2005 | Greenhalgh |
| 6,994,724 B2 | 2/2006 | Schmitt |
| 7,122,052 B2 | 10/2006 | Greenhalgh |
| 7,226,474 B2 | 6/2007 | Iancea et al. |
| 7,550,004 B2 | 6/2009 | Bahler et al. |
| 7,582,110 B2 | 9/2009 | Case et al. |
| 7,758,626 B2 | 7/2010 | Kim et al. |
| 8,287,586 B2 | 10/2012 | Schaeffer et al. |
| 8,696,733 B2 | 4/2014 | Bogert et al. |
| 9,427,306 B2 | 8/2016 | Shahriari |
| 9,492,268 B2 | 11/2016 | Winner et al. |
| 9,827,086 B2 | 11/2017 | Winner et al. |
| 2003/0196717 A1 | 10/2003 | Nunez et al. |
| 2005/0131516 A1 | 6/2005 | Greenhalgh |
| 2005/0154446 A1 | 7/2005 | Phillips et al. |
| 2009/0282908 A1 | 11/2009 | Homayoun |
| 2012/0165918 A1* | 6/2012 | Du ............................ A61F 2/07 623/1.15 |
| 2013/0184808 A1 | 7/2013 | Hall et al. |
| 2015/0320542 A1 | 11/2015 | Gabriele |
| 2016/0270897 A1 | 9/2016 | Whiting |
| 2016/0305050 A1 | 10/2016 | Winner |
| 2017/0105854 A1 | 4/2017 | Treacy et al. |
| 2018/0202082 A1 | 7/2018 | Van Hulle |
| 2020/0058991 A1 | 2/2020 | Adugna et al. |
| 2020/0289253 A1* | 9/2020 | Sumanasinghe .......... A61F 2/07 623/1.13 |

FOREIGN PATENT DOCUMENTS

| | | | |
|---|---|---|---|
| DE | 10043291 A1 * | 4/2001 | ............... D03D 3/02 |
| EP | 0095940 A2 | 12/1983 | |
| EP | 0175554 A2 | 3/1986 | |
| GB | 2115776 A | 9/1983 | |
| JP | H 03-45743 A | 2/1991 | |
| WO | WO 83/03349 | 10/1983 | |
| WO | WO 88/06026 | 8/1988 | |
| WO | WO 89/00031 | 1/1989 | |
| WO | WO 97/43983 | 11/1997 | |
| WO | WO 2008/008528 A2 | 1/2008 | |
| WO | WO 2017/014830 A1 | 1/2017 | |

OTHER PUBLICATIONS

Extended European Search Report for European Application No. 21275047.5 dated Sep. 6, 2021 (7 pages).

Extended European Search Report for European Application No. 19194707.6 dated Jan. 21, 2020 (9 pages).

* cited by examiner

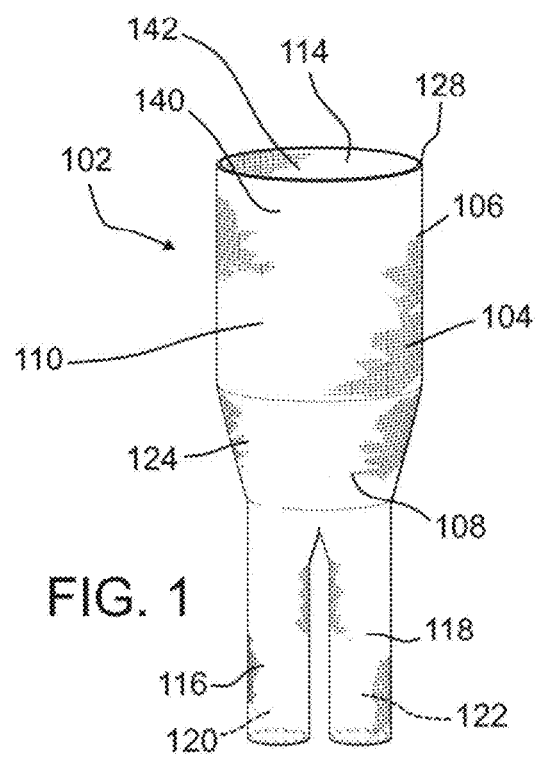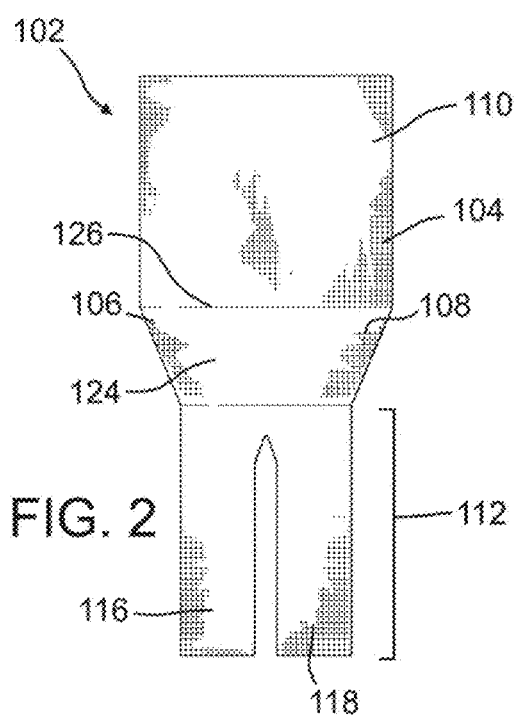

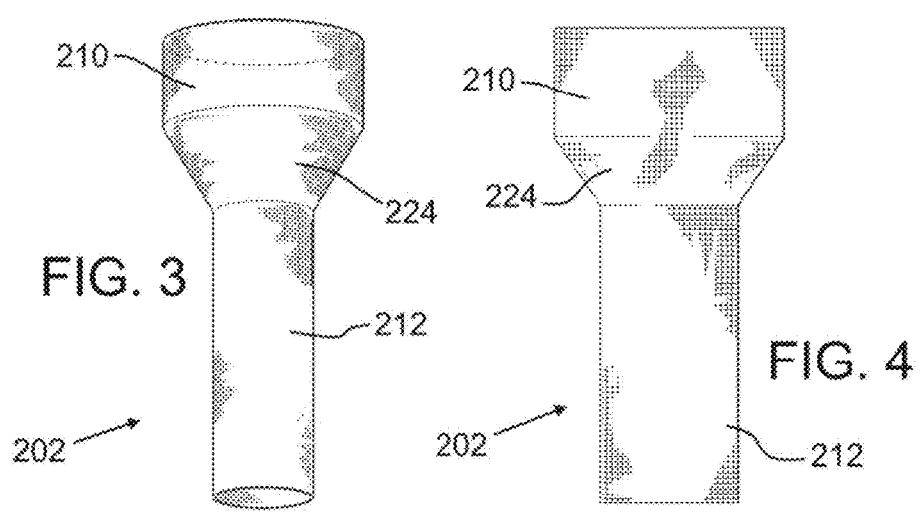

FIG. 6

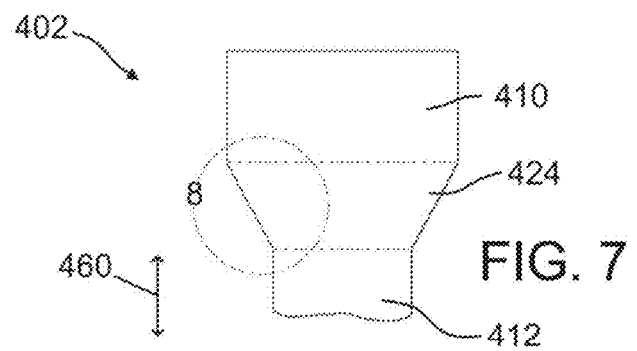
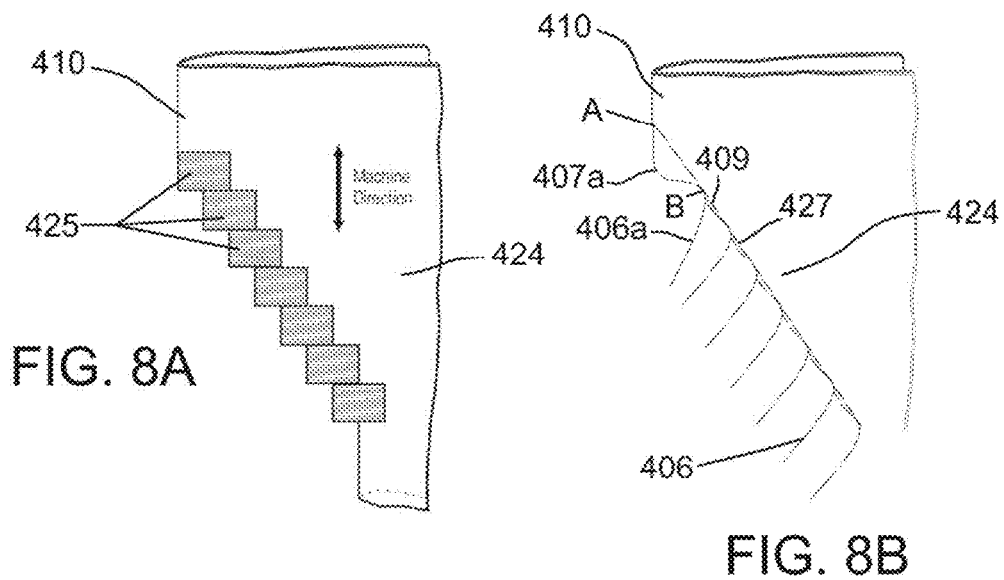

WOVEN GRAFT HAVING A TAPER WITH A RE-ENGAGED WARP END

RELATED APPLICATIONS

This application claims the benefit of U.S. Provisional Application No. 63/016,662, filed Apr. 28, 2020, which is hereby incorporated by reference in its entirety.

BACKGROUND

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

Woven fabrics are useful in the construction of grafts due to their desirable mechanical properties and the ease and low cost of manufacturing such fabrics. However, existing woven fabrics cannot include certain shapes, such as tapers, without compromising the structural integrity of such fabrics (e.g., due to the potential for fraying) and/or without adding unwanted structures (such as certain seams). In view of this background, the present disclosure provides an improved woven graft material for use in a stent graft.

BRIEF DESCRIPTION OF THE DRAWINGS

The embodiments will be further described in connection with the attached drawings. It is intended that the drawings included as a part of this specification be illustrative of the exemplary embodiments and should in no way be considered as a limitation on the scope of the present disclosure. Indeed, the present disclosure specifically contemplates other embodiments not illustrated but intended to be included in the claims.

FIG. 1 is an illustration showing a front perspective view of a bifurcated graft having a woven taper in accordance with certain aspects of the present disclosure.

FIG. 2 is an illustration showing a front, flattened view of the bifurcated graft of FIG. 1.

FIG. 3 is an illustration showing a front perspective view of another embodiment of a graft having a taper in accordance with certain aspects of the present disclosure.

FIG. 4 is an illustration showing a front, flattened view of the graft of FIG. 3.

FIG. 6 is an illustration showing a weaving diagram (e.g., point diagram) of the design set-up for the sequence of FIG. 5.

FIG. 7 is an illustration showing a portion of a woven graft having a woven taper formed by the sequence depicted in FIG. 5.

FIG. 8A is an illustration showing a close-up view about section 8 of FIG. 7, and particularly showing a series of tapered subsections in accordance with certain aspects of the present disclosure.

FIG. 8B is an illustration showing a close-up view about section 8 of FIG. 7, and particularly showing the configuration of certain warp ends along an edge of the taper immediately after weaving in accordance with certain aspects of the present disclosure.

FIG. 10 is an illustration showing a weaving diagram (e.g., point diagram) of the design set-up for the sequence of FIG. 9.

FIG. 12 is an illustration showing a weaving diagram (e.g., point diagram) of the design set-up for the sequence of FIG. 11.

DETAILED DESCRIPTION

Figure 5:
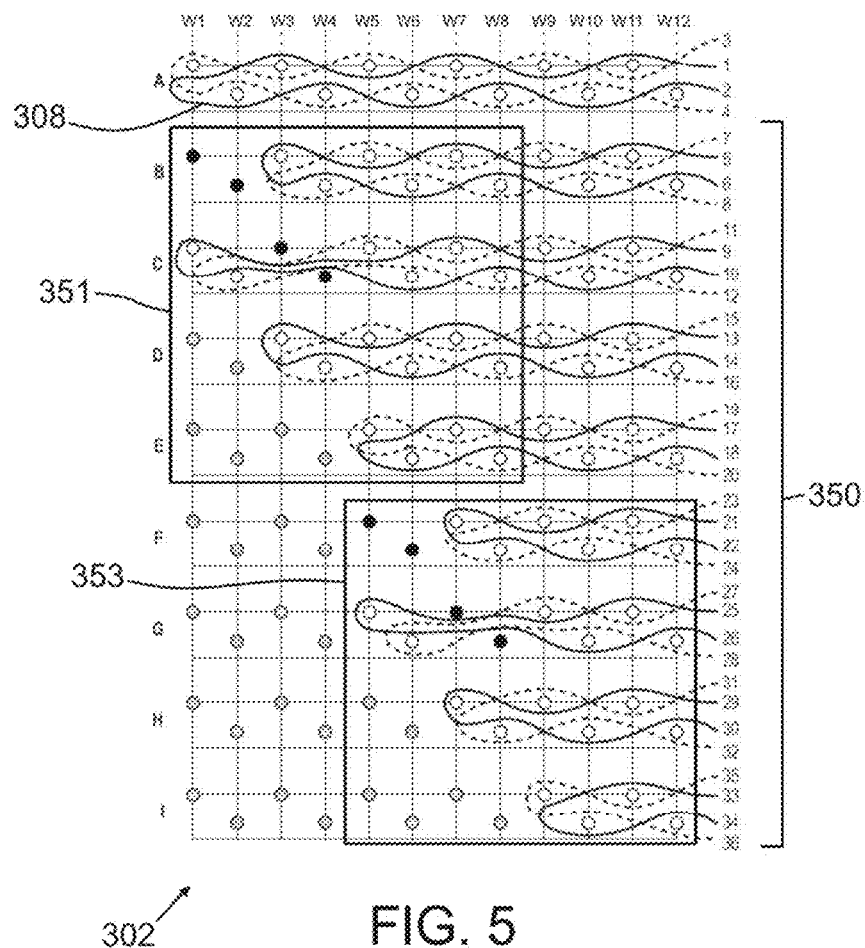
FIG. 5 is an illustration showing a diagram depicting certain weaving steps that indicate how the yarns are interlaced to form a woven taper in accordance with certain aspects of the present disclosure.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, biliary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis. The term "stent graft" as used herein refers to a prosthesis comprising a stent and a graft material associated therewith that forms a lumen through at least a portion of its length.

Woven fabrics are useful in the construction of grafts due to their desirable mechanical properties and the ease and low cost of manufacturing such fabrics. Existing woven fabrics cannot include certain shapes, such as tapers, without compromising the structural integrity of such fabrics (e.g., due to the potential for fraying) and/or without adding unwanted structures (such as certain seams). The embodiments described herein, and variations thereof, provide a novel way of forming a tapered graft with a weaving machine and the resulting graft and stent-graft structures. Such graft material may be advantageously used with stents of various shapes. These teachings are advantageous for allowing woven graft material to be used with stent grafts of various shapes and sizes (e.g., configured for deployment for particular target areas within a human or animal body). The embodiments herein, and variations thereof, may include any suitable feature described in U.S. patent application Ser. No. 16/553,394 (and corresponding Publication No. 2020/0069411), filed Aug. 28, 2019, and titled "GRAFT HAVING AT LEAST ONE WOVEN TAPER," which is hereby incorporated by reference in its entirety.

FIG. 1 is an illustration showing a top view of a tubular woven graft 102, which may be an implantable graft for implantation to a patient body. FIG. 2 is an illustration showing a view of the flattened top layer of tubular graft of FIG. 1. As shown in FIGS. 1-2, the graft 102 may be a portion of a stent graft, and thus the graft 102 may be associated with a stent (not shown). Further, the graft 102 may be a woven graft having walls formed substantially of a woven fabric 104. The woven fabric 104 may have a plurality of warp yarns (depicted as "warp ends 106") aligned substantially in a first direction that are interwoven with a plurality of weft threads or yarns (e.g., weft yarns 108) aligned substantially in a second direction, where the first direction and the second direction are substantially perpendicular. For example, the warp ends 106 may be the lengthwise threads attached to a loom before weaving begins, and the warp ends 106 may be manipulated by a reed during the weaving process. The weft yarns 108 (also known as woof or fill yarns) may be the strands that are shuttled back and forth across the warp ends 106 such that the warp ends 106 and the weft yarns 108 together define the woven fabric 104.

As shown, the graft 102 may include a main tubular section 110 and a bifurcated section 112. The main tubular section 110 may be configured for deployment in a vessel or other body lumen, such as an aorta of a human (or other) patient to treat an aneurysm. To allow blood flow through the main tubular section 110, a main lumen 114 may extend through the entire tubular woven graft that is constructed in the form of woven fabric 104.

The bifurcated section 112, which also may be formed with the tubular woven fabric 104, may extend from the main tubular section 110. In exemplary embodiment, the bifurcated section 112 may include a first branch 116 and a second branch 118 for deployment within branch vessels extending from the aorta (e.g., the iliac arteries of a human or other patient). The bifurcated section 112 may extend distally from the main tubular section 110, but it may alternatively extend a different direction from the main tubular section 110 in other embodiments. The bifurcated section 112 may include a first branch 116 and a second branch 118 (and in some embodiments, more than two branches may be included). To allow blood flow through the branches, the first branch 116 and the second branch 118 may include a first branch lumen 120 and a second branch lumen 122 (respectively) in fluid communication with the main lumen 114 of the main tubular section 110.

Optionally, the main tubular section 110 may include a tapered portion 124 at its distal end 126 that extends from a cylindrical portion 128. The tapered portion 124 may be frustoconical in shape and may decrease in diameter as it extends distally from the cylindrical portion 128 of the main tubular section 110. The tapered portion 124 may be advantageous to providing a smooth transition from the main tubular section 110 to the bifurcated section 112. For example, when the graft 102 is configured for use in and around the aorta, the tapered portion 124 may provide a smooth transition between the abdominal aorta and the common iliac arteries, but tapers for other body locations are also contemplated. In other embodiments, the main tubular section 110 may lack the tapered portion 124, and thus the bifurcated section 112 may extend directly from the cylindrical portion 128. When the tapered portion 124 is included, it may be formed with a woven structure as described in more detail below.

Similarly, the bifurcated section 112 may include a tapered section (not shown) where at least one of the branches includes a tapered structure. For example, the first branch 116 may include a first branch taper and the second branch may include a second branch taper (not shown). If included, the first branch taper and the second branch taper may each include a respective frustoconical wall that surrounds the first branch lumen 120 and the second branch lumen 122, respectively. Advantageously, the first branch taper and/or the second branch taper (if included) may provide a smooth transition from a main vessel (e.g., the abdominal aorta) to smaller respective branch vessels.

Tapered sections may also be included in grafts that lack a bifurcated portion. For example, FIGS. 3-4 are an illustration showing another embodiment of a tubular woven graft 202. In this embodiment, the graft 202 includes a first tubular section 210 and a second tubular section 212, where the second tubular section 212 has a smaller diameter than the first tubular section 210. A tapered portion 224 may be located between the first tubular section 210 and the second tubular section 212. The graft 202 of FIGS. 3-4 may be configured (e.g., sized and shaped) for treating an aneurysm in iliac arteries of the human leg, for example.

For the above-described examples, variations thereof, and other tapered grafts, the tapered geometry may be formed with a unique and novel weaving technique, where particular warp yarns are selectively removed from the engagement with the corresponding weft threads while weaving and then re-engaged later before being permanently released. The below figures describe such a process and certain resulting structure.

FIG. 5 shows a weaving sequence with weaving steps A-I. Within the weaving steps A-I are a plurality of weft insertions 1-36, where each weft insertion includes shuttling or otherwise inserting a weft yarn 308 such that it is interwoven with at least a portion of a set of warp ends comprising the depicted warp ends W1-12. While twelve (12) warp ends W1-W12 are used in this example, more or fewer may be used. For example, the number of warp ends may be optimized to provide a graft of a suitable size having a taper with a suitable length and angle.

In Step A, a first weft insertion 1 forms a portion of a first layer of the graft 302 with a weft yarn 308 (e.g., the first layer 140 of the graft 102 of FIG. 1). When this same weft yarn 308 returns (at weft insertion 2), the weft yarn 308 forms a second layer that is separable from the first layer such that a cavity is formed therebetween (e.g., the second layer 142 of the graft 102 of FIG. 1 thereby forming the main lumen 114). After the second weft insertion 2, a third weft insertion 3 is performed using the warp yarns of the first layer followed by a fourth weft insertion 4 that uses the warp yarns of the second layer. The third weft insertions 3 and 4 may utilize the previously-used weft thread (i.e., from weft insertions 1-2) or alternatively a new weft thread (or both). One key feature is that throughout the entirety of the steps depicted in FIG. 5 the warp ends associated with the weft insertion 1 and weft insertion 3 remain separate from those associated with weft insertion 2 and weft insertion 4 (i.e., via selective harness action on the loom), which ensures that the lumen of the graft 302 is not interrupted. However, it is contemplated that these warp ends may be mixed at areas near the edge of the graft 302 to enhance securement of the layers.

While only the leftmost twelve (12) warp ends W1-W12 are shown, the pattern shown in step A may be repeated to the right of warp end W1 such that a graft having a suitable width/diameter is achieved. Further, if step A is repeated, a non-tapered length of the graft may be formed. Thus, step A of FIG. 5 may be repeated numerous times such that the non-tapered length of the graft (e.g., main tubular section 110 of FIG. 1, for example) is suitable for a particular medical function.

Step B of FIG. 5 initiates a first tapered portion 350, where the width and diameter of the graft 302 begin to shrink in size along the lengthwise direction of the graft 302. As shown, the weft insertions 5-8 do not engage the terminal warp ends, which at this stage of the sequence are warp ends W1-W2. Otherwise, the weft insertions 5-8 may have substantially the same characteristics of the prior weft insertions 1-4 (e.g., such that the texture of the outer surface of the graft remains substantially the same).

At step C, the recently-dropped warp ends W1-W2 are re-engaged (via weft insertions 9-12), thereby re-introducing the warp ends W1-W2 into the woven structure. Advantageously, this step improves the quality of the seam between the first layer and the second layer (e.g., reduced porosity and increased durability without adding bulkiness) since the loose warp ends W1-W2 including an extra engagement with the woven structure (and therefore an additional point of securement) prior to leaving the structure entirely. Further, the re-introduced warp ends W1-W2 may be located in front of an area that may otherwise include a pore or other small opening due to the dropping of a different warp end (e.g., one or more of warp ends W3-W4 as discussed below).

Optionally, step C may drop another set of warp ends, in this instance the warp ends W3-W4. Alternatively, this step may occur further downstream in the sequence. However, advantageously, by dropping the warp ends W3-W4 with the same weft insertions (i.e., weft insertion 9-12) that re-engage the warp ends W1-W2, the re-engaged portions of the warp ends W1-W2 may at least partially cover an opening forming as a result of dropping warp ends W3-W4.

In step D (and beyond), the warp ends W1-W2 are wholly excluded. In one or more post processing steps (typically after weaving is complete), the warp ends W1-W2 may be trimmed from the graft at a location corresponding to step D (as discussed below), and in some circumstances may be heat sealed, sealed with an adhesive, or otherwise locked in place to prevent unraveling.

Step D also functions to re-engage the warp ends W3-W4 (e.g., in a manner similar to the re-engagement of warp ends W1-W2 in step C), and in step E (and beyond), the warp ends W3-W4 are wholly excluded. Thus, in a similar fashion, the warp ends W3-W4 may be trimmed from the graft at a location corresponding to step E and locked in place as needed.

Step E of FIG. 5 is similar to step A, but the resulting structure is smaller in diameter/width. In particular, step E forms a two-layer woven structure utilizing fewer weft threads than step A. If step E is repeated, a constant-diameter (or constant-width) portion of the graft 302 will be formed (specifically between the first tapered subsection 351 and a second tapered subsection 353), and such repetitions may be desirable in certain embodiments.

Figure 6:
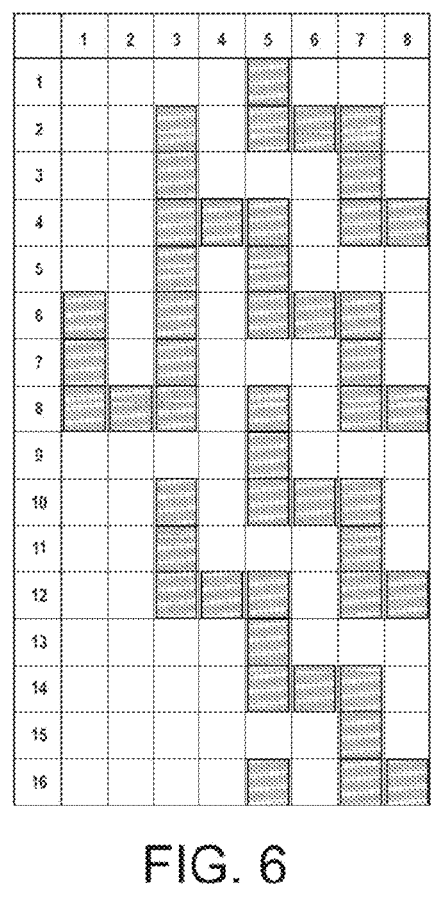

Steps F-I of FIG. 1 are similar to steps B-E. For example, in these steps, warp ends W5-W6 and warp ends W7-W8 are dropped in a similar manner to warp ends W1-W2 and warp ends W3-W4 in steps B-E, respectively. In other words, steps B-E are repeated during steps F-I but with an off-set of the already dropped or removed warp yarns W1-W4 to generate a continuous taper. As a result, a second tapered portion 350 is formed. Afterwards, step I may be repeated to form a constant-diameter (or constant-width) portion of the graft 302 (e.g., the second tubular section 212 of FIG. 2 for example). Alternatively, a series of weaving steps similar to those of steps B-E and steps F-I may be repeated to form a third tapered portion, thereby extending the length of the taper and further reducing the diameter/width of the graft 302. FIG. 6 is a diagram of the point design set-up for weaving the graft 302 corresponding to FIG. 5, which is a type of setup diagram understood by those with ordinary skill in the art.

The technique described above (of FIG. 5) may be used to form a taper 424 of a graft 402, as shown in FIG. 7. In particular, the taper 424 may reduce the cross-sectional size of the graft 402 in the longitudinal direction 460 between a first graft portion 410 and a second graft portion 412, where the first graft portion 410 has a diameter that is larger than a diameter of the second graft portion 412. To provide the taper 424 with a suitable size, certain weaving steps may be repeated as necessary. Thus, by adapting the sequence to a particular design, the taper 424 may be configured (e.g., sized, positioned, and angled) such that the graft 402 is properly sized for use in a specific area of a human or animal body.

As shown in FIG. 8A for example, seven tapered subsections 425 combine to form the taper 424 of FIG. 7. Each of the seven tapered portions 424 may incorporate steps similar or identical to those discussed above (e.g., in accordance with steps B-E of FIG. 5, for example). More or fewer than seven tapered portions 424 may be formed. In some embodiments, the tapered subsections 425 may be directly adjacent to each other, but one or more may alternatively be spaced apart.

FIG. 8B is another illustration depicting the taper 424 of FIG. 7, which shows a diagram illustrating the configuration of certain warp ends 406 along the edge of the tapered portion 424. Notably, FIG. 8B is not to scale (as certain features may appear much smaller in a real-world application, including relative to the angle of the tapered portion 424). As shown in FIG. 8A, a warp end 406a may be secured to corresponding weft threads (not shown individually) at a location A. At a location B, the warp end 406a may re-engage with weft threads forming the tapered portion 424 of the graft material. Between location A and location B, the warp end 406 may include a floating portion 407a that "skips," or bypasses, the weft threads in the tapered portion 424. Optionally, this floating portion 407a may have some slack (as shown) such that it is loose relative to the weft threads, but in other embodiments it may be substantially taught (e.g., substantially lacking slack). Advantageously, the floating portion 407a may cover a discontinuity 409 that may be formed where the floating portion 407a initially exits the woven fabric, thereby reducing the porosity of the edge 427 of the tapered portion 424. Once released at location B, the warp end 406b may be related permanently (and optionally, the loose end may be trimmed during a post-weaving process). The other depicted warp ends 406 may be similarly oriented along the edge 427.

Figure 9:
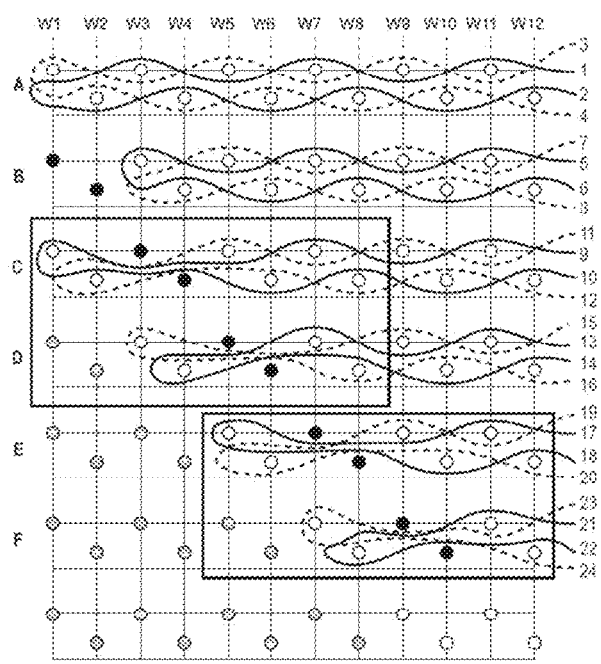
FIG. 9 is an illustration showing another diagram depicting certain weaving steps that indicate how the yarns are interlaced to form a woven taper in accordance with certain aspects of the present disclosure.

FIG. 9 shows another example of a weaving sequence for forming a taper. Steps A-C of FIG. 9 are depicted as being identical to steps A-C of FIG. 5 (although certain variations may be included). In each of the progressive steps of the sequence (steps D, E, F, etc.), the warp ends that were previously dropped are re-engaged, a new set of warp ends is dropped, and the previously re-engaged warp ends are dropped permanently. For example, in step D, the warp ends W3-W4 are re-engaged (after being dropped in the prior step), warp ends W5-W6 are initially dropped, and warp ends W1-W2 are dropped for a second time (and permanently, in this instance).

Figure 10:
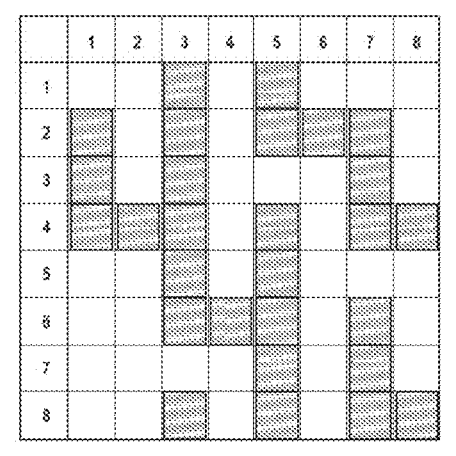

Step E, step F, and step G repeat this sequence with the next-available warp ends while progressively moving towards the center of the graft 102. The end result is a woven taper similar to that of FIGS. 7-8B. However, since the sequence of FIG. 9 moves to a new set of warp ends at each step (rather than including intervening weaving steps, such as steps D-E in FIG. 5), the taper formed by the sequence of FIG. 9 may be steeper (i.e., the angle between the lengthwise direction of the taper and the longitudinal direction of the graft may be greater). Any of the steps of FIG. 9 (and variations thereof) may be altered to achieve a desirable taper length and/or taper angle. FIG. 10 shows a diagram of the point design set-up for weaving the sequence of FIG. 9.

Figure 11:
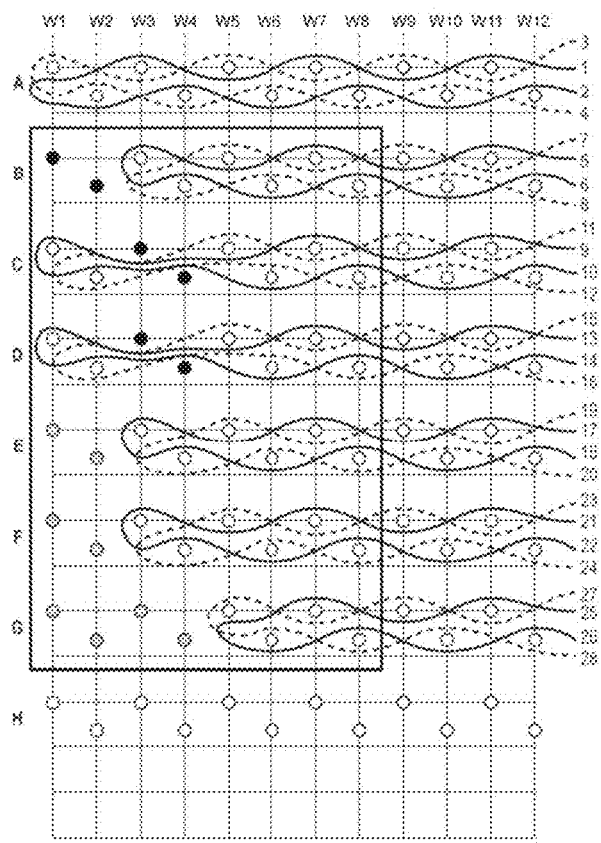
FIG. 11 is an illustration showing another diagram depicting certain weaving steps that indicate how the yarns are interlaced to form a woven taper in accordance with certain aspects of the present disclosure.
Figure 12:
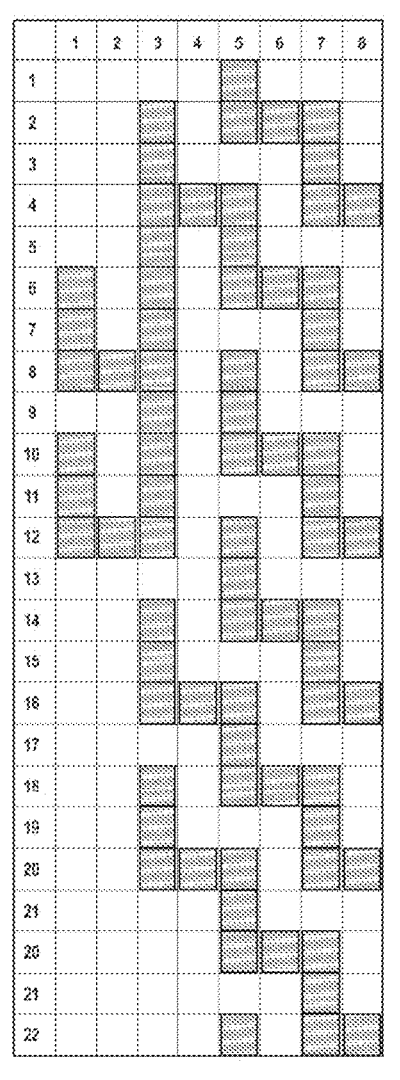

FIG. 11 shows another example of a weaving sequence for forming a taper. Steps A-C of FIG. 11 are depicted as being identical to step A of FIG. 5 (although certain variations may be included). Step D is a repetition of step C. Advantageously, the re-engaged warp ends W1-W2 may be re-woven into the seam multiple times (e.g., engaged with multiple weft threads), which may enhance the securement of the warp ends W1-W2, thereby adding durability to the woven taper. While the warp ends W1-W2 re-engage through four weft insertions (i.e., depicted weft insertions 9-16), more or fewer may be included. Similarly, in steps E-F, the previously-dropped warp ends W3-W4 are re-woven into the seam multiple times. At step G (which may be repeated as necessary), non-tapered tubular weaving may continue. However, depending on the taper size, steps B-F may be repeated as necessary. FIG. 12 is a diagram of the design set-up for weaving the graft 102 corresponding to FIG. 11.

In the above-depicted examples, the tapers are formed with a substantially linear profile. Other shapes are also contemplated (e.g., by altering the weaving sequences below, for example). FIGS. 13-18 show certain non-liming embodiments of curved tapers.

Figure 14:
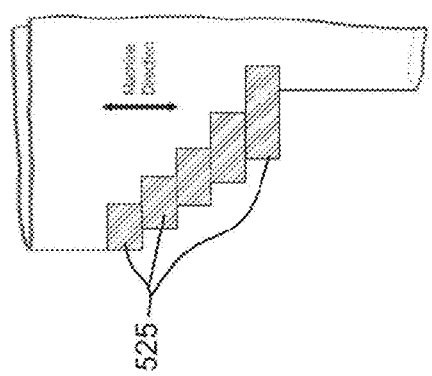
FIG. 14 is an illustration showing a series of tapered subsections from the embodiment of FIG. 13 in accordance with certain aspects of the present disclosure.
Figure 13:
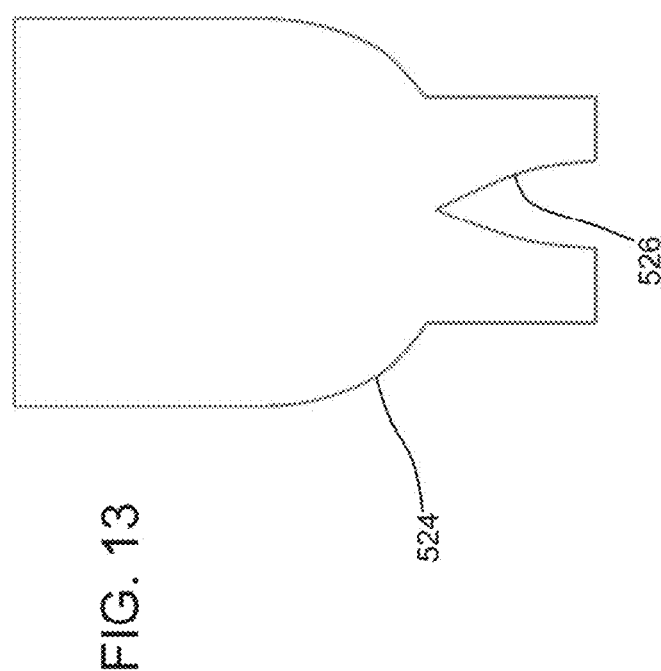
FIG. 13 is an illustration showing another embodiment of a bifurcated graft having a curved taper in accordance with certain aspects of the present disclosure.
Figure 15:
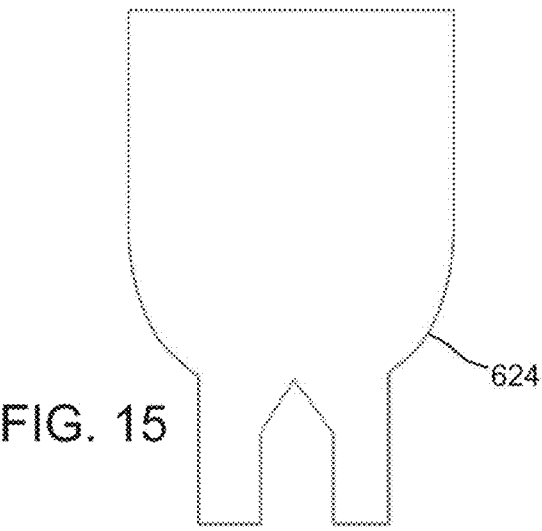
FIGS. 15-19 are illustrations showing various embodiments of grafts having at least one curved taper in accordance with certain aspects of the present disclosure.
Figure 16:
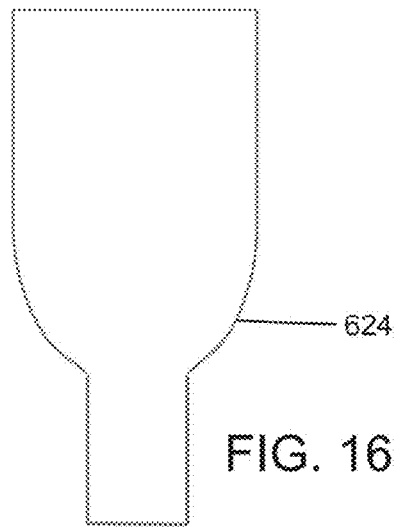
Figure 17:
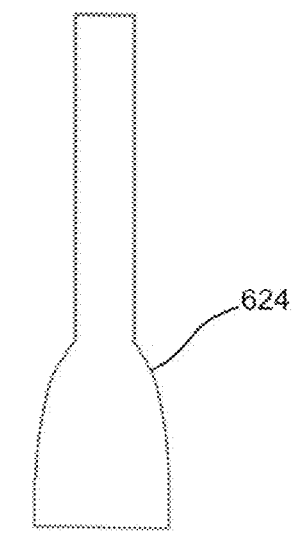
Figure 18:
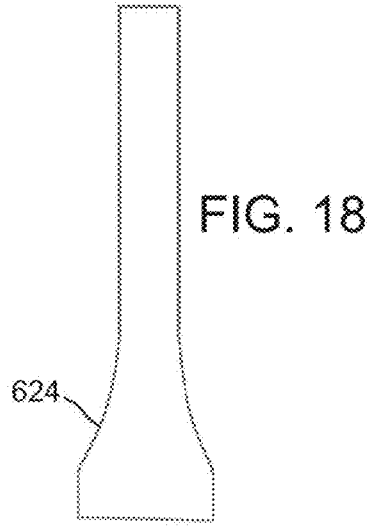
Figure 19:
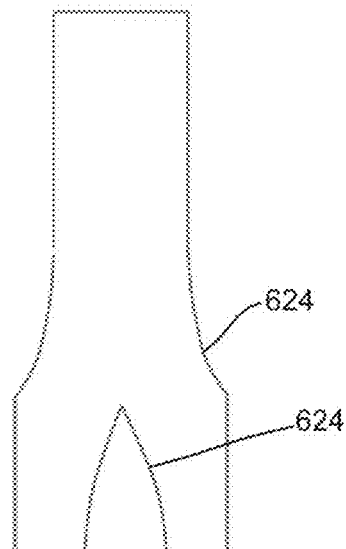

FIG. 13, for example, shows a graft having a curved taper 524. The curved taper 524 may be formed using a weaving technique similar to those described above, but where the taper angle (e.g., the angle of the tapered edge) changes along the taper's length. This may be created by changing the woven construction of the taper along the taper's length. For example, the weaving steps for forming the embodiment of FIG. 13 are shown in FIG. 14. As shown in FIG. 14, the lower tapered subsections 525 (e.g., similar to the subsections 425 shown in FIG. 8A) include a larger taper angle than higher tapered sections 525. Once completed, this gradual increase in taper angle along the taper's length (e.g., moving from the higher taper subsections 525 in FIG. 14 to the lower taper subsections 525) will cause curvature. Similar curved tapers may be located in other locations, such as at the second curved taper 526. FIG. 15-19 show other non-limiting examples of locations where curved tapers 625 may be desirable (e.g., which may be convex or concave relative to an exterior surface of the graft). Such curved tapers may be added at any suitable location in a graft, including certain embodiments that are not shown.

Without limitation, the subject matter of this disclosure may also relate to one or more of the following aspects (and combinations thereof). These aspects, and features thereof, may be combined (where suitable).

In a first aspect, a tubular graft is included for use in a stent graft. Without limitation, the graft may include one or more of the following features: a first woven layer, where the first woven layer forms a first side of the tubular graft, the first woven layer having a set of first warp ends; a second woven layer, where the second woven layer forms a second side of the tubular graft, the second woven layer having a set of second warp ends, where the set of second warp ends is distinct from the set of first warp ends; and a tapered portion having an edge, where the edge connects the first woven layer and the second woven layer, where the tapered portion includes a first weft thread, a second weft thread, and a third weft thread, the second weft thread being between the first weft thread and the third weft thread, where each of the first weft thread, the second weft thread, and the third weft thread extends through the first woven layer and the second woven layer, where the first weft thread and the third weft thread engage a first warp end at the edge of the tapered portion such that the first warp end is secured to the edge at the first weft thread and the third weft thread, and where a floating portion of the first warp end extends from the first weft thread to the third weft thread such that the floating portion bypasses the second weft thread.

A free end of the first warp end may extend from the edge of the tapered portion.

At least two weft threads may secure the first warp end to the edge at a location between the floating portion of the first warp end and the free end of the first warp end.

The edge of the tapered portion may be located between the floating portion of the first weft thread and a lumen within the tapered portion of the tubular graft.

The graft may further include a second warp end, where the second warp end engages a fourth weft thread and a sixth weft thread, where a second floating portion of the second warp end bypasses a fifth weft thread, and where the fifth weft thread is located between the fourth weft thread and the sixth weft thread.

The floating portion of the first warp end may bypass at least three weft threads.

The floating portion of the first warp end may bypass at least five weft threads.

The first warp end may be heat sealed to the edge of the tapered portion.

At least a portion of the edge of the tapered portion may be curved.

A second aspect includes a method for forming a graft. The method may include one or more of the following steps: weaving a first woven layer that forms a first side of the graft, the first woven layer having a set of first warp ends; weaving a second woven layer that forms a second side of tubular graft, the second woven layer having a set of second warp ends, where the set of second warp ends is distinct from the set of first warp ends; and weaving a tapered portion having an edge, where the edge connects the first woven layer and the second woven layer, where the tapered portion includes a first weft thread, a second weft thread, and a third weft thread, the second weft thread being between the first weft thread and the third weft thread, where each of the first weft thread, the second weft thread, and the third weft thread extends through the first woven layer and the second woven layer, where the first weft thread and the third weft thread engage a first warp end at the edge of the tapered portion such that the first warp end is secured to the edge at the first weft thread and the third weft thread, and where a floating portion of the first warp end extends from the first weft thread to the third weft thread such that the floating portion bypasses the second weft thread.

A free end of the first warp end may extend from the edge of the tapered portion.

At least two weft threads may secure the first warp end to the edge at a location between the floating portion of the first warp end and the free end of the first warp end.

The edge of the tapered portion may be located between the floating portion of the first weft thread and a lumen within the tapered portion of the graft.

The graft may further includes a second warp end, where the second warp end engages a fourth weft thread and a sixth weft thread, where a second floating portion of the second warp end bypasses a fifth weft thread, and where the fifth weft thread is located between the fourth weft thread and the sixth weft thread.

The floating portion of the first warp end may bypass at least three weft threads.

The floating portion of the first warp end may bypass at least five weft threads.

The method may further include heating the edge of the tapered portion to permanently secure the first warp end to the edge.

In a third aspect, a tubular graft for use in a stent graft may include a woven tapered portion, the woven tapered portion having an edge that extends along a decreasing-diameter portion of the tubular graft, where the tapered portion includes a first weft thread, a second weft thread, and a third weft thread, the second weft thread being between the first weft thread and the third weft thread, where the first weft thread and the third weft thread engage a first warp end at the edge of the tapered portion such that the first warp end is secured to the edge at the first weft thread and the third weft thread, and where a floating portion of the first warp end extends from the first weft thread to the third weft thread such that the floating portion bypasses the second weft thread.

A free end of the first warp end may extend from the edge of the tapered portion, where at least two weft threads secure the first warp end to the edge at a location between the floating portion of the first warp end and the free end of the first warp end.

The edge of the tapered portion may be located between the floating portion of the first weft thread and a lumen within the tapered portion of the tubular graft. While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A tubular graft for use in a stent graft, the tubular graft comprising:
    a first woven layer, wherein the first woven layer forms a first side of the tubular graft, the first woven layer having a set of first warp ends;
    a second woven layer, wherein the second woven layer forms a second side of the tubular graft, the second woven layer having a set of second warp ends, wherein the set of second warp ends is distinct from the set of first warp ends; and
    a tapered portion having an edge, wherein the edge connects the first woven layer and the second woven layer,
    wherein the tapered portion includes a first weft thread, a second weft thread, and a third weft thread, the second weft thread being between the first weft thread and the third weft thread,
    wherein each of the first weft thread, the second weft thread, and the third weft thread extends through the first woven layer and the second woven layer,
    wherein the first weft thread and the third weft thread engage a first warp end at the edge of the tapered portion such that the first warp end is secured to the edge at the first weft thread and the third weft thread,
    wherein a floating portion of the first warp end extends from the first weft thread to the third weft thread such that the floating portion bypasses the second weft thread, and
    wherein a first set of warp ends are selectively removed from engagement with a first set of weft threads and then later re-engaged with a second set of weft threads before being permanently released, such that a seam established between the first layer and second layer is provided with enhanced characteristics.

2. The tubular graft of claim 1, wherein a free end of the first warp end extends from the edge of the tapered portion.

3. The tubular graft of claim 2, wherein at least two weft threads secure the first warp end to the edge at a location between the floating portion of the first warp end and the free end of the first warp end.

4. The tubular graft of claim 1, wherein the edge of the tapered portion is located between the floating portion of the first weft thread and a lumen within the tapered portion of the tubular graft.

5. The tubular graft of claim 1, further comprising a second warp end, wherein the second warp end engages a fourth weft thread and a sixth weft thread, wherein a second floating portion of the second warp end bypasses a fifth weft thread, and wherein the fifth weft thread is located between the fourth weft thread and the sixth weft thread.

6. The tubular graft of claim 1, wherein the floating portion of the first warp end bypasses at least three weft threads.

7. The tubular graft of claim 1, wherein the floating portion of the first warp end bypasses at least five weft threads.

8. The tubular graft of claim 1, wherein the first warp end is heat sealed to the edge of the tapered portion.

9. The tubular graft of claim 1, wherein at least a portion of the edge of the tapered portion is curved.

10. A tubular graft for use in a stent graft, the tubular graft comprising:
  a woven tapered portion, the woven tapered portion having an edge that extends along a decreasing-diameter portion of the tubular graft,
  wherein the tapered portion includes a first weft thread, a second weft thread, and a third weft thread, the second weft thread being between the first weft thread and the third weft thread,
  wherein the first weft thread and the third weft thread engage a first warp end at the edge of the tapered portion such that the first warp end is secured to the edge at the first weft thread and the third weft thread, and
  wherein a floating portion of the first warp end extends from the first weft thread to the third weft thread such that the floating portion bypasses the second weft thread, and
  wherein a first set of warp ends are selectively removed from engagement with a first set of weft threads and then later re-engaged with a second set of weft threads before being permanently released, such that a seam established between the first layer and second layer is provided with enhanced characteristics.

11. The tubular graft of claim 10, wherein a free end of the first warp end extends from the edge of the tapered portion, and wherein at least two weft threads secure the first warp end to the edge at a location between the floating portion of the first warp end and the free end of the first warp end.

12. The tubular graft of claim 10, wherein the edge of the tapered portion is located between the floating portion of the first weft thread and a lumen within the tapered portion of the tubular graft.

* * * * *